(12) United States Patent
Pandit

(10) Patent No.: US 9,265,651 B2
(45) Date of Patent: Feb. 23, 2016

(54) LOADING, INSERTING AND RELEASING TOOL FOR AN INTRAUTERINE DEVICE

(75) Inventor: Nishma Pandit, Pune (IN)

(73) Assignee: Pregna International Limited, Pune (IN)

( * ) Notice: Subject to any disclaimer, the term of this patent is extended or adjusted under 35 U.S.C. 154(b) by 567 days.

(21) Appl. No.: 13/303,568

(22) Filed: Nov. 23, 2011

(65) Prior Publication Data

US 2013/0068234 A1    Mar. 21, 2013

(30) Foreign Application Priority Data

Sep. 19, 2011   (IN) .......................... 2642/MUM/2011

(51) Int. Cl.
*A61F 6/18* (2006.01)
*A61F 6/14* (2006.01)
*A61F 6/00* (2006.01)
*A61F 6/06* (2006.01)

(52) U.S. Cl.
CPC . *A61F 6/144* (2013.01); *A61F 6/00* (2013.01); *A61F 6/06* (2013.01); *A61F 6/14* (2013.01); *A61F 6/18* (2013.01)

(58) Field of Classification Search
CPC ............... A61F 6/00; A61F 6/06; A61F 6/08; A61F 6/12; A61F 6/14; A61F 6/144; A61F 6/18

See application file for complete search history.

(56) References Cited

U.S. PATENT DOCUMENTS

| 3,783,861 A | * | 1/1974 | Abramson ..................... 128/840 |
| 3,918,444 A | * | 11/1975 | Hoff et al. ..................... 128/840 |
| 3,965,891 A | * | 6/1976 | Lerner .......................... 128/840 |
| 4,143,656 A | * | 3/1979 | Holmes ........................ 128/840 |
| 4,249,525 A | * | 2/1981 | Krzeminski ............. A61F 6/18 |
| | | | 128/840 |

* cited by examiner

*Primary Examiner* — Keri J Nelson

(74) *Attorney, Agent, or Firm* — Wiley Rein LLP

(57) ABSTRACT

An embodiment in accordance with the present invention provides a loading, inserting and releasing tool for T-shaped intrauterine device (IUD) into a uterus. The loading tool comprises a shaft member having a loader, an inserter tube, an IUD and a plunger. The loading tool includes a platform configured at a proximal end of the loader for holding the IUD in an open position, and an elongated member extending from the platform. The elongated member includes a slot running therethrough aligned to the opening of the loader. Further, the loading tool includes a plunger within an inserter tube capable of running through a slot provided with markings thereon. The inserter tube is provided with a knob for pushing the inserter tube along with plunger in forward and backward direction for inserting and releasing the T-shaped IUD into the uterus.

5 Claims, 4 Drawing Sheets

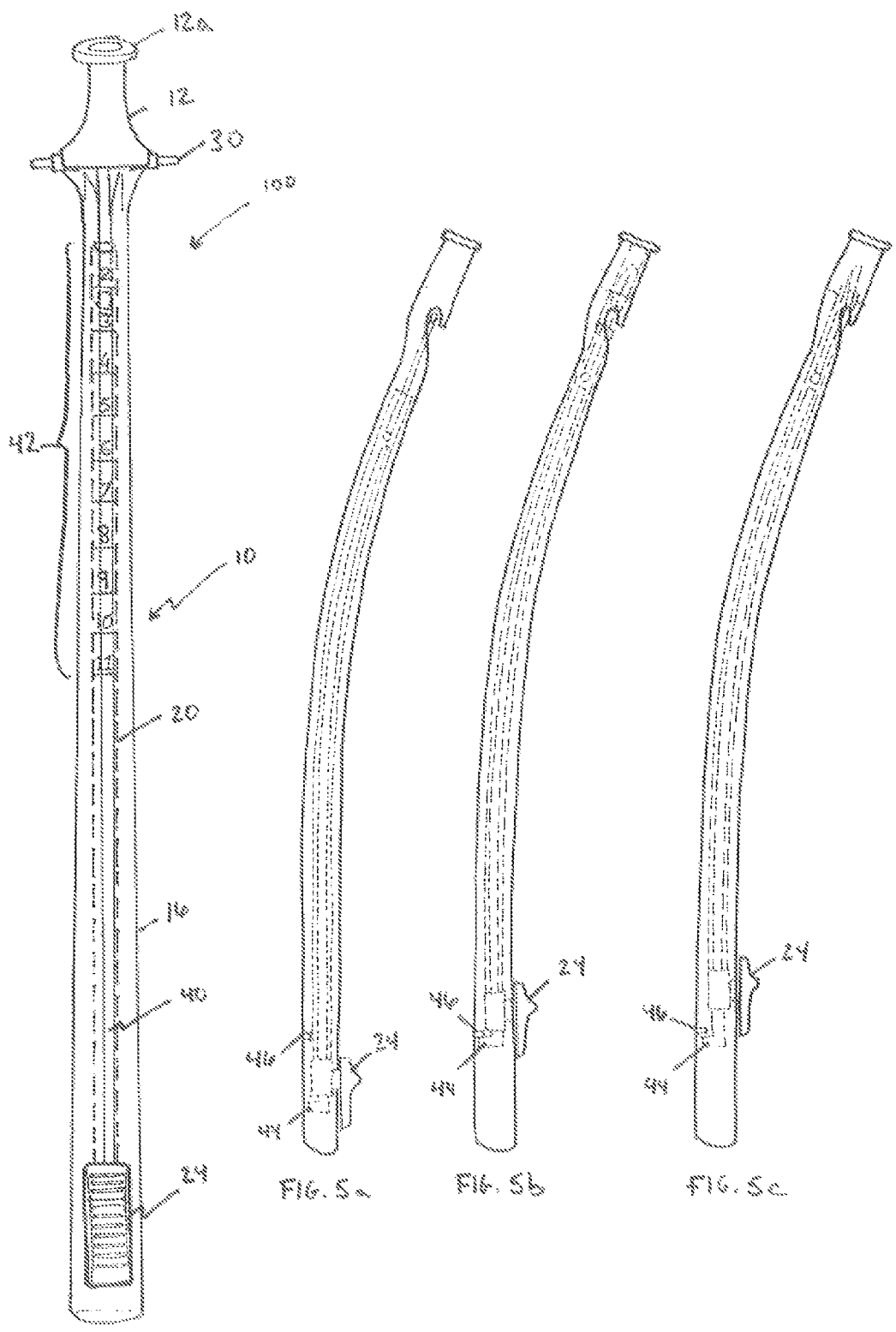

LOADING, INSERTING AND RELEASING TOOL FOR AN INTRAUTERINE DEVICE

CROSS-REFERENCE TO RELATED APPLICATIONS

This application claims priority to Indian Patent Application No. 2642/MUM/2011, filed Sep. 19, 2011, priority is claimed to this application and the disclosure of this application is incorporated by reference in its entirety.

FIELD OF INVENTION

The present invention relates to a loading tool for assisting in insertion and release of an intrauterine device into a uterus, and more specifically, to a loading, insertion and release tool of a T-shaped intrauterine device into a uterus.

BACKGROUND OF THE INVENTION

Conventionally, loading mechanism for an intrauterine contraceptive device (hereinafter 'IUD') includes devices where a Copper T (hereinafter 'Cu T') is loaded into a tube manually by hand and then the tube is inserted into a uterus. Further, the release of the Cu T in the uterus is also controlled manually. However, the loading devices which are small, needs to be handled by both the hands. The handling of such devices is to be done cautiously and skillfully. Further, handling of two or many loose parts is involved while using the conventional loading devices. Further, such handling may a cause infection. The physicians would need both the hands to be used for insertion of the IUD with the help of the conventional loading means which makes it difficult to handle other tools simultaneously and may even lead to improper loading, improper insertion, misaligned IUD placement. In such cases, physicians have to depend on assistants to hold the tools.

Furthermore, the existing loading devices are very straight and may not follow the natural curve of the human body making it painful and difficult to use. Also, the release of the Cu T in the uterus needs to be well controlled by the physician and in case of wrong usage, the relative movement between the solid rod (plunger) of the loading means and the tube may cause injury to the patient.

Moreover, the numbers of steps involved in executing the insertion of the IUD using conventional loading devices are many and may confuse the physician and the physician needs training and practice in order to use the device.

Some embodiments of the invention may provide a loading, inserting and releasing for IUD which provides a trouble free insertion and release and provide high level of safety to the doctors as well as patients.

Some embodiments of the invention may provide a loading, inserting and releasing for IUD which requires minimum steps to be performed for insertion of the intrauterine device in the uterus.

Some embodiments of the invention may provide a single use loading, inserting and releasing tool for an IUD.

Some embodiments of the invention may provide a loading, inserting and releasing for an IUD which is less painful as compared to a conventional IUD loading device.

Some embodiments of the invention may provide a ergonomic tool for the doctors.

SUMMARY OF THE INVENTION

Accordingly, an embodiment of the present invention may provide a loading, inserting and releasing tool for a T-shaped intrauterine device (IUD) into a uterus.

The loading tool comprises: a shaft member comprising, a loader having a flange configured at a front portion thereof, a platform configured at a proximal end of the loader, the platform configured to hold the T-shaped IUD in an open position in front of an opening of the loader, and an elongated member extending from the platform, the elongated member having a slot running therethrough, wherein the slot is aligned to the opening of the loader; an inserter tube having a lower portion of the T-shaped IUD inserted therein, the inserter tube having marking thereon; a plunger configured within the inserter tube for supporting the lower portion of the T-shaped IUD, the inserter tube along with the plunger configured to run through the slot; and a knob configured on the inserter tube, the knob enables movement of the inserter tube along with plunger in forward and backward direction, wherein, upon placing the T-shaped IUD on the platform in an open position, the knob is pushed forward up to a predetermined marking on the inserter tube thereby pushing horizontal arms of the T-shaped IUD in a folded position inside the loader and thereafter in the inserter tube, and positioning the T-shaped IUD in folded position, at a premeasured size as per the markings, thereafter the inserter tube is inserted into the uterus up to a predetermined depth and the knob is pulled backwards thereby releasing the T-shaped IUD into the uterus from the folded position to the open position.

Typically, wherein folding and engaging of the horizontal arms of the T-shaped IUD inside the inserter tube is achieved by the loader and the integrated snaps and stoppers.

Typically, wherein a conical channel is provided for facilitating the folding of the horizontal arms of the T-shaped intrauterine device inside the inserter tube.

Typically, wherein the elongated member has a curve which provides comfort to a patient and the doctor while inserting the loading means.

Typically, wherein the inserter tube has scale marking on it depicting the measurement of depth of uterus.

BRIEF DESCRIPTION OF THE DRAWINGS

FIG. 4 is another view of the loading tool of FIG. 1.

FIGS. 5a through 5c depict the advancement of the inserter tube.

DETAIL DESCRIPTION OF AN EMBODIMENT OF THE INVENTION

The foregoing problems and shortcomings associated with the prior art techniques and approaches are overcome by the some embodiments of present invention as described below in the preferred embodiment.

An embodiment of the present invention provides a loading tool for intrauterine device (IUD) which provides a trouble free insertion and high level of safety to the user. Further, the loading tool requires minimum steps to be performed for insertion of the IUD in the uterus. Furthermore, the loading tool for the IUD is less painful for the patient and easy for the doctor as compared to conventional IUD loading device.

The illustrated embodiment is shown with reference to the accompanying drawings, throughout which reference numbers indicate corresponding parts in the figure. These reference numbers are shown in bracket in the following description.

Figure 1:
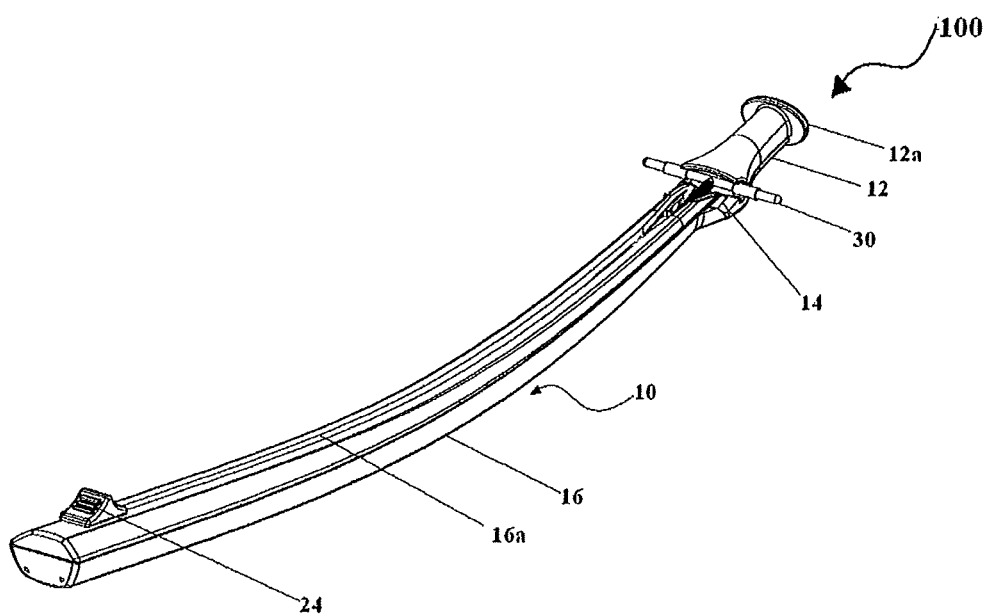
FIG. 1 depicts a perspective view of a loading tool for inserting an intrauterine device (IUD) into a uterus, in accordance with the present invention.
Figure 2:
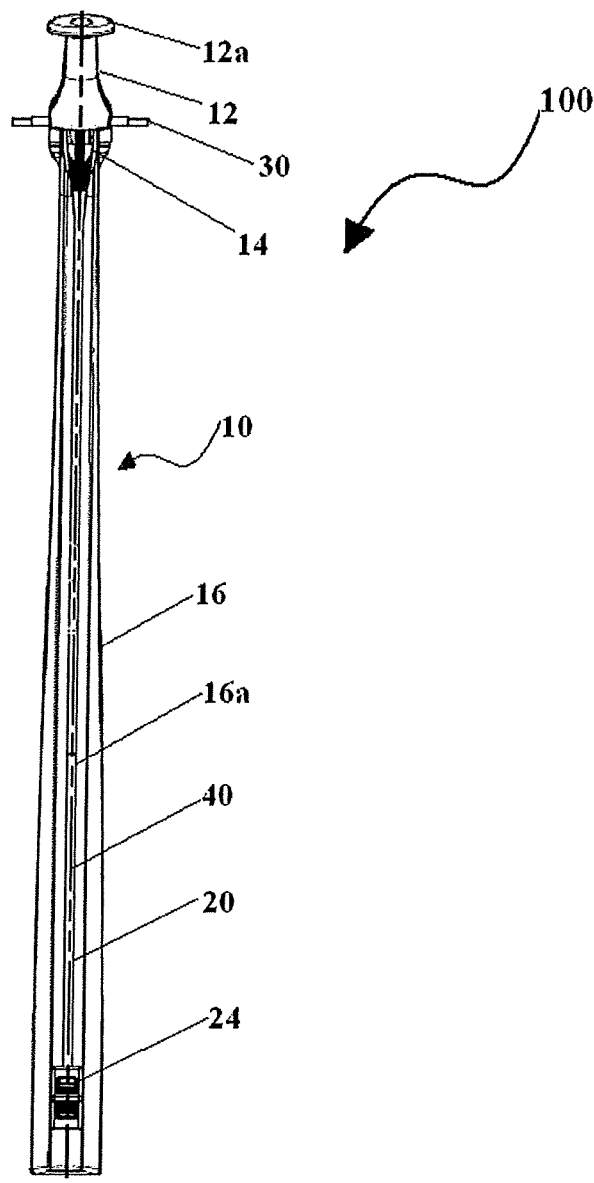
FIG. 2 depicts a top view of the loading tool of FIG. 1.
Figure 3:
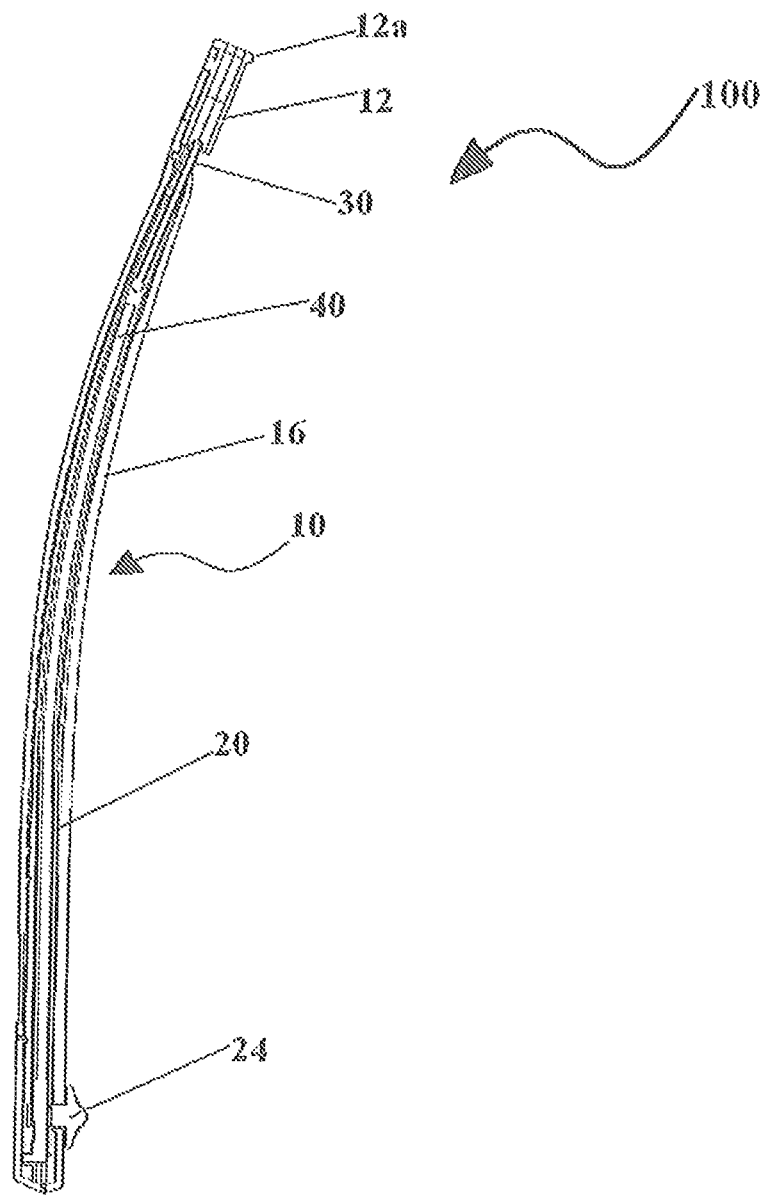
FIG. 3 depicts a cross sectional view of the loading tool of FIG. 1.

Referring now to FIGS. 1-3, there are shown various views of a loading tool for insertion of a T-shaped intrauterine device (hereinafter IUD) into a uterus, in accordance with the present invention. Specifically the FIGS. 1-3 show a loading tool 100. The loading tool 100 includes a shaft member 10, an inserter tube 20, a T-shaped IUD 30 and a plunger 40.

The shaft member 10 includes a loader 12. The loader 12 is configured to receive a T-shaped IUD 30 therein in a folded form. In an embodiment, the T-shaped IUD is a Copper-T. Further, the loader includes a flange 12a provided on a front portion thereof. The flange 12a restricts the entry of the loader 12 into the uterus.

At the proximal end of the loader 12, there is provided a platform 14. The platform 14 is capable of holding the T-shaped IUD 30 in an open position in front of an opening (not numbered) of the loader 12.

The shaft member 10 further includes an elongated member 16 extending from the platform 14. The elongated member 16 has a slot 16a running therethrough covering the entire length of the elongated member 16. In an embodiment, the slot 16a is partially closed. Specifically, the slot 16a is aligned to the opening of the loader 12. In an embodiment, the elongated member has a natural curve to help user and a patient to feel comfortable while inserting the loading tool 100 in the uterus.

Further, the inserter tube 20 includes a lower portion of the T-shaped IUD 30 inserted therein prior to the operation of loading, inserting and releasing the T-shaped IUD 30 in to the uterus. The inserter tube 20 is provided with markings 42 (see FIG. 4) thereon and is capable of running through the slot 16a.

Furthermore, a knob 24 is provided on the inserter tube 20 for pushing the inserter tube 20 in forward and backward direction. Specifically, the markings 42 on the inserter tube 20 helps the physician to position the inserter tube 20 to a predetermined length in the uterus. Generally, the length of the uterine cavity varies from patient to patient. The length of the uterine cavity is measured by a uterine sound or any other uterine length measuring equipment known in the art. In an embodiment, when the inserter tube is pushed forward, a click sound is generated due to the protrusions or snaps 44, 46 (see FIGS. 5a-5c) which facilitate one way movement of the plunger 40. This is useful to the doctor in case they are unable to visually see the reading or in case they are not looking at the markings 42 during the positioning.

The plunger 40 is configured within the inserter tube 20 for supporting the lower portion of the T-shaped IUD 30. Specifically, the inserter tube 20 along with the plunger 40 is capable of running through the slot 16a.

In an operation, the T-shaped IUD 30 is placed on the platform 14 in an open position. Thereafter, the knob 24 is pushed forward to predetermined marking 42 thereby pushing horizontal arms of the T-shaped IUD 30 in a folded position inside the inserter tube 20 with the help of the loader 12 integrated snaps and stoppers 44, 46. Further, a cone in the loader 12 is provided for facilitating the folding of the horizontal arms of the T-shaped intrauterine device inside the inserter tube.

Furthermore, the loading tool 100 is pushed through vaginal cavity up to the mouth of the uterus wherein the loader flange 12a restricts the further movement of the loader 12 inside the uterus. The loader 12 holds the T-shaped IUD in front of the uterus in folded position inside the inserter tube 20. Thereafter, the loading tool 100 is further pushed so that the inserter tube 20 enters into the uterus up to a predetermined depth identified by the doctor by use of the uterine sound or any similar device and then the knob 24 is pulled backwards thereby releasing the T-shaped IUD 30 into the uterus from the folded position to the open position. Specifically, the pulling back of the knob 24 pulls back the inserter tube 20, however, the plunger 40 remains in place which helps to release the T-shaped IUD 30 from folded position to the open position in the uterus.

The loading tool 100 is a single hand operated device which can be used with extreme ease. Further, the loading tool 100 is a single use loading tool for an IUD which provides a clean process of insertion of an IUD without having chance of infection. The mechanism of the loading tool 100 ensures that it is single time use as the stoppers placed on the inside prevent re-use. Further, the curve of the loading tool 100 has been derived from the natural curve of the human body and has been kept subtle to accommodate variations in shape, position and change in sizes. The design of the loading tool 100 is comfortable to hold in the palm of the physician.

The foregoing descriptions of specific embodiments of the present invention have been presented for purposes of illustration and description. They are not intended to be exhaustive or to limit the present invention to the precise forms disclosed, and obviously many modifications and variations are possible in light of the above teaching. The embodiments were chosen and described in order to best explain the principles of the present invention and its practical application, to thereby enable others skilled in the art to best utilize the present invention and various embodiments with various modifications as are suited to the particular use contemplated. It is understood that various omission and substitutions of equivalents are contemplated as circumstance may suggest or render expedient, but such are intended to cover the application or implementation without departing from the spirit or scope of the present invention.

I claim:

1. A loading, inserting and releasing tool for placement of a T-shaped intrauterine device (IUD) into a uterus, the loading tool comprising:
   a shaft member comprising:
      a loader having a flange configured at a front portion thereof,
      a platform configured at a proximal end of the loader, the platform configured to hold the T-shaped IUD in an open position in front of an opening of the loader, and
      an elongated member extending from the platform, the elongated member having a slot running therethrough, wherein the slot is aligned to the opening of the loader;
   an inserter tube having a lower portion of the T-shaped IUD inserted therein, the inserter tube having markings thereon;
   a plunger configured within the inserter tube for supporting the lower portion of the T-shaped IUD, the inserter tube along with the plunger configured to run through the slot; and
   a knob configured on the inserter tube, the knob enabling movement of the inserter tube along with the plunger in a forward direction and a backward direction,
   wherein, upon placement of the T-shaped IUD on the platform in the open position, movement of the knob in the forward direction forces horizontal arms of the T-shaped IUD into a folded position inside the loader and positions the horizontal arms of the T-shaped IUD in the folded position in the inserter tube; and
   wherein after the inserter tube is inserted into the uterus up to a predetermined depth, movement of the knob in the backward direction releases the T-shaped IUD into the uterus from the folded position to the open position, and wherein the loading tool is configured for insertion into the vaginal cavity.

2. The loading tool of claim 1, wherein the knob and the plunger further include integrated snaps and stoppers configured to help engage the horizontal arms of the T-shaped IUD for placement of the T-shaped IUD into the folded position inside the inserter tube.

3. The loading tool of claim 1, wherein a conical channel is provided for facilitating the folding of the horizontal arms of the T-shaped intrauterine device inside the inserter tube.

4. The loading tool of claim 1, wherein the elongated member has a curve configured to provide comfort a patient and the doctor during usage of the loading tool.

5. The loading tool of claim 1, wherein the markings on the inserter tube depict a measurement of depth of the uterus.

* * * * *